(12) United States Patent
Shealy

(10) Patent No.: US 7,364,753 B2
(45) Date of Patent: Apr. 29, 2008

(54) MAGNESIUM-CONTAINING COMPOSITIONS AND METHODS FOR ENHANCING DEHYDROEPIANDROSTERONE LEVELS

(76) Inventor: C. Norman Shealy, 5607 S. 222nd Rd., Fair Grove, MO (US) 65648

( * ) Notice: Subject to any disclaimer, the term of this patent is extended or adjusted under 35 U.S.C. 154(b) by 735 days.

(21) Appl. No.: 10/690,927

(22) Filed: Oct. 22, 2003

(65) Prior Publication Data

US 2005/0089581 A1    Apr. 28, 2005

(51) Int. Cl.
*A61K 9/14*    (2006.01)
(52) U.S. Cl. .................. 424/488; 424/400; 424/401
(58) Field of Classification Search ............... 424/422, 424/401; 514/557, 63
See application file for complete search history.

(56) References Cited

U.S. PATENT DOCUMENTS

| 4,744,924 | A | 5/1988 | Hensen et al. |
|---|---|---|---|
| 4,943,432 | A | 7/1990 | Biener |
| 5,141,741 | A | 8/1992 | Ishida et al. |
| 5,420,118 | A * | 5/1995 | Alban et al. ................... 514/63 |
| 5,609,617 | A | 3/1997 | Shealy et al. |
| 5,804,168 | A | 9/1998 | Murad |
| 5,891,853 | A | 4/1999 | Shealy et al. |
| 5,922,764 | A * | 7/1999 | Cantin et al. ............... 514/557 |
| 6,287,548 | B1 | 9/2001 | Biener |
| 6,471,972 | B1 | 10/2002 | Bonte et al. |

* cited by examiner

*Primary Examiner*—Michael G. Hartley
*Assistant Examiner*—James Rogers
(74) *Attorney, Agent, or Firm*—Foley & Lardner LLP

(57) ABSTRACT

Compositions and methods for using the same to restore dehydroepiandrosterone (DHEA) levels in humans are described. The compositions comprise magnesium chloride, a suitable solvent, a gelling agent and a glycerin. The compositions are administered to the skin of humans to enhance DHEA levels through the transdermal absorption of magnesium. The compositions can be administered in various forms, including as a lotion, an ointment, or as a bath additive.

10 Claims, No Drawings

MAGNESIUM-CONTAINING COMPOSITIONS AND METHODS FOR ENHANCING DEHYDROEPIANDROSTERONE LEVELS

FIELD OF THE INVENTION

This invention pertains to compositions and methods for using the same to enhance serum levels of dehydroepiandrosterone ("DHEA") in human beings without administration of exogenous dehydroepiandrosterone or salts thereof.

BACKGROUND OF THE INVENTION

Dehydroepiandrosterone, also known as prasterone, 3-hydroxyandrost-5-en-17-one, dehydroisoandrosterone, trans-dehydroandrosterone, or $\Delta^5$-androsten-3-$\beta$ol-17-one (referred to hereinafter as "DHEA"), is a 17-ketosteroid, which is quantitatively one of the major adrenocortical steroid hormones present in the metabolism of humans and other mammals. S. Budavari, ed., Merck Index, Eleventh Edition (1989). This endogenous androgenic steroid has been shown to have a myriad of biological activities. An assortment of prior art has recognized the plethora of beneficial effects of DHEA, its sulfate ester (DHEA-S) and salts thereof. DHEA is readily interconvertible in vivo with DHEA-S through the action of intracellular sulfatases.

In U.S. Pat. No. 4,920,115 to Nestler et al., oral dosages of DHEA given to healthy male individuals were shown to reduce body fat mass, increase muscle mass, lower LDL cholesterol levels without affecting HDL cholesterol levels, and not affect tissue sensitivity to insulin in human patients. Nestler et al. described the use of pharmaceutical preparations of DHEA as a preventative means to avoid development of atherosclerosis.

U.S. Pat. Nos. 5,110,810 and 5,162,198 issued to Eich et al., disclose methods for treating human beings with pharmacological quantities of DHEA, resulting in increased serum DHEA and DHEA-S in their blood, which lowers rates of platelet aggregation. By reducing the rate of platelet aggregation, the incidence of morbidity and mortality from vascular events such as myocardial infarction and stroke, as well as the occurrence of restenosis following vascular interventions, can be significantly reduced.

U.S. Pat. No. 4,835,147 to Roberts demonstrated that administration of DHEA or its therapeutically acceptable salts to individuals ameliorated symptoms of prostatic hypertrophy, certain symptoms of menopause, particularly those related to nervous system dysfunction, and of psychosexual dysfunction, symptoms such as inhibited sexual desire, inhibited sexual excitement and inhibited orgasm.

Other widely varying medical uses for DHEA have been reported. U.S. Pat. No. 4,628,052, issued to Peat, reports using either an oral or topical preparation of DHEA to treat rheumatoid arthritis, osteo-arthritis and arthritis associated with psoriasis and with lupus and other auto-immune diseases, and also for treating non-specific joint pain associated with stress or incidental to other ailments.

DHEA compounds have also been established to have a beneficial effect as an anti-diabetic agent. See U.S. Pat. No. 4,518,595 to Coleman et al.

In the medical literature, many favorable reports of medical benefits to individuals due to increased levels of DHEA and its sulfate ester, DHEA-S, have been reported as well. Geriatrics 37:157 (1982) stated that DHEA was a "miracle" drug, which may prevent obesity, aging, diabetes mellitus and heart disease. Barrett-Conner et al. produced studies which revealed an inverse relationship between cardiovascular death and serum DHEA-S levels in adult men. N. Engl. J. Med. 315:1519 (1986). Arad et al. in Arteriosclerosis 9:159 (1989) and Gordon et al. in J. Clin. Invest 82:712 (1988) both describe the reduction of atherosclerosis plaque formation by DHEA.

One of the most important uses of DHEA has been to improve the immune response in human beings. U.S. Pat. No. 5,077,284, issued to Loria et al., describes the administration of DHEA, either orally or by subcutaneous injection, to provide very high levels of protection against viral, bacterial, fungal or parasitic infections in immuno-compromised animals and humans. The experimental animal data, described by Loria et al., demonstrated that in infection (100,000 plaque forming units/animal) of a human coxsackievirus B4 strain, which causes mortality in about 90% of infected animals, mortality was reduced to 37% when animals were treated with DHEA. Moreover, Loria et al. demonstrated that administration of DHEA induced an 80% elevation in the number of antibody forming cells within the animal. In virus infected and DHEA treated animals, there was also an elevation in the number of monocyte cells, the particular white blood cells associated with a resistance to coxsackievirus infection. This elevation was not observed in uninfected animals that were treated with DHEA. This observation demonstrates that DHEA can be used to up-regulate the host immune response to virus infection, by increasing the number of antibody forming cells, elevating the number of white blood cells associated with resistance to virus infection and markedly reducing virus induced mortality.

Although DHEA is the most abundantly produced adrenal steroid and serum concentrations of its sulfate ester, DHEA sulfate (DHEA-S), are approximately 20 fold higher than those of any other circulating steroid hormone, levels of this hormone begin to decline within individuals during the second decade of life, reaching 5% of the original level in the elderly.

Peak serum DHEA and DHEA-S levels occur when a patient is approximately 25 years old and decline over the ensuing decades. Ohrentreich et al. found that mean DHEA-S levels and ranges for adult men were as follows: Ages 25-29 (3320 ng/ml); ages 45-49 (1910 ng/ml); ages 65-69 (830 ng/ml). See J. Clin. Endocrinol. Metab., 59:551 (1984). Similar age related decline in serum DHEA-S levels were found to occur in women. Correspondingly, the incidence of cardiovascular disease in human beings increases with age, thus suggesting an epidemiological relationship between serum DHEA and DHEA-S levels in cardiovascular disease. In Barrett-Conner et al., supra, the baseline DHEA-S levels of 242 middle aged men (ages ranging between 50 and 79 years) was compared to the subsequent 12 year mortality rate of the men from any cause, from cardiovascular disease, and from ischemic heart disease. DHEA-S levels were significantly lower in men with a history of heart disease compared to those without. In men with no history of heart disease, the age-adjusted relative risk associated with DHEA-S levels below 140 µg/dl was 1.5 (p NS) for death from any cause, 3.3 (p<0.05) for deaths from cardiovascular disease, and 3.2 (p<0.05) for deaths from ischemic heart disease. An increase in DHEA-S level of 100 µg/l had a 48% reduction in mortality (adjusted for other risk factors) from cardiovascular disease (p<0.05).

Further Eich et al. supra, demonstrated that treating human beings with pharmacological quantities of DHEA resulted in increased serum levels of DHEA and DHEA-S.

Eich et al. performed in vivo experiments using a test group of 10 male human being subjects. In these experiments, DHEA was administered in a double-blind placebo controlled trial in an amount of 300 mg of DHEA per day in the form of 100 mg capsules taken orally 3 times a day. The study found that the initial baseline serum DHEA prior to conducting the experiment was 5.83+/−3.9 ng/ml, and the mean serum DHEA during the second week of investigation for the placebo group was 5.58+/−4.1 ng/ml. The mean serum DHEA for the treated group during the second week investigation was 28.7+/−13.9 ng/ml. In addition, the baseline serum DHEA-S was 316.2 µg/dl and during the second week, the mean serum DHEA-S level was 260.5+/−56.7 µg/dl in the placebo group, and 1451.9+/−56.7 µg/dl in the DHEA group. Elevation of serum DHEA-S levels when a patient is receiving only supplemental DHEA suggested that DHEA-S serves as a storage pool for DHEA, which is the active form of the hormone. The rate of platelet aggregation for the human subjects participating in this study was examined prior to treatment with supplemental DHEA and was again tested on three different occasions during the second week of an investigation. Four of the five test subjects who received the DHEA supplement demonstrated a slower rate of aggregation and a requirement for higher concentration of arachidonic acid to initiate aggregation. Thus, the elevated serum DHEA level slowed platelet aggregation which can significantly reduce the incidence of morbidity and mortality from vascular events such as myocardial infarction and stroke.

SUMMARY OF THE INVENTION

The present invention provides compositions and methods for using the same for enhancing or restoring DHEA in an individual through transdermal absorption of magnesium. Because DHEA is a naturally occurring steroid, it has been found that endogenous production of the hormone may be stimulated by these compositions and methods, without the use of pharmaceutical preparations containing DHEA, its sulfate ester DHEA-S, or salts thereof.

One object of the invention is to provide compositions for elevating serum DHEA levels in an individual, which compositions comprise therapeutically effective amounts of magnesium chloride in combination with a suitable solvent, a gelling agent and glycerin.

DETAILED DESCRIPTION OF THE PREFERRED EMBODIMENTS

It has been found that DHEA levels may be raised in human beings through transdermal absorption of magnesium without the application of exogenous supplements of DHEA, DHEA-S, or their corresponding salts. Treatments consisting of applying a composition comprising a therapeutically effective amount of magnesium chloride, a suitable solvent, a gelling agent and glycerin to the skin of an individual have been surprisingly and unexpectedly found to increase production of DHEA.

Stimulating natural biosynthesis of DHEA within the body is advantageous over the heretofore known methods of raising serum DHEA levels which consisted of administering DHEA, DHEA-S, or salts thereof, either parenterally, intravenously, subcutaneously, or transdermally. Clinical studies of treatments involving administration of DHEA, its esters, or salts thereof, have shown undesirable side effects associated with administration of the hormone. These side effects include mild androgenic effects and hirsutism. See W. Regelson et al., New York Academy of Sciences, 518:260 (1988). Side effects from the ingestion of DHEA, and other undesirable consequences involving the method of DHEA administration, can be avoided with the method of the present invention. No side effects have been detected from utilization of the present invention to raise DHEA levels in patient's blood.

The effective compositions herein described have been found to raise serum DHEA levels in human beings. These compositions comprise a therapeutically effective amount of magnesium chloride salts in a suitable solvent combined with a gelling agent and glycerin. As used herein, a therapeutically effective amount is an amount sufficient to increase DHEA levels in a human being when applied daily over a period of at least 1 week, and desirably over a period of at least about four weeks. The ingredients may be mixed together in a blender and are desirably, but not necessarily, stored in a container of a micoid laminar crystal for a period of time (e.g. at least 3 days) prior to application. A typical composition will include about 15 to 35 weight percent (wt. %) magnesium chloride. This includes compositions that contain about 20 to 30 wt. % magnesium chloride and further includes compositions that contain about 25 to 35 wt. % magnesium chloride. Although other salts may be present in the compositions, in some embodiments it is desirable for the compositions to be substantially free of mineral salts other than magnesium chloride. For the purposes of this disclosure, a composition may be considered substantially free of additional salts if that composition comprises no more than about 2 wt. %, desirably no more than about 1 wt. % and more desirably no more than about 0.1 wt. % of the additional salts. In some embodiments, the composition is free from any mineral salts other than magnesium chloride. In particular, it may be desirable for the compositions to be free or substantially free of sodium ions. It is believed that these sodium ions, which are readily absorbed through the skin, compete and interfere with the transdermal aborption of the magnesium. Notably, it has been found that magnesium chloride may not be simply substituted with another magnesium-containing salt to achieve the same effect. For example, compositions containing magnesium sulfate rather than magnesium chloride did not have similar effects on DHEA levels. It is believed that this may be attributed to the size of the sulfate ion, which is larger than chloride, and therefore may hinder transdermal absorption of the magnesium sulfate. Thus, in some embodiments, the composition is free of or substantially free of sulfate ions and/or magnesium sulfate.

In the composition, the magnesium chloride is dissolved in any suitable solvent capable of dissolving sodium chloride crystals. Typically the solvent will be water. In some embodiments of the composition, the solvent makes up about 55 to 80 wt. % of the composition. This includes compositions wherein the solvent makes up about 60 to 75 wt. % of the composition and further includes embodiments where the solvent makes up about 65 to 70 wt. % of the composition.

In addition to the magnesium chloride and the solvent, the compositions contain one or more gelling agents which serve to provide the compositions with a consistency that renders them easily applicable to the skin of an individual. Typically, the gelling agent will be present in an amount of about 0.1 to 5 wt. % and desirably about 1 to 3 wt. %. Suitable gelling agents include, but are not limited to, celluloses, such as methyl cellulose.

The compositions further include glycerin to provide a smooth feel upon application to the skin. The glycerin content of the compositions will typically range from about 0.5 to 5 wt. % and desirably from about 1 to 3 wt. %.

The compositions may optionally contain additional additives typically found in skin treatments including, but not limited to, soaps, perfumes and dyes.

The compositions can be applied to the skin in various formulations, such as lotions, ointments, or bath additives. The amount of the composition which is sufficient to be effective for enhancing serum DHEA levels will vary with the individual being treated and is ultimately at the discretion of the medical practitioner. The factors to be considered include the exact nature of the formulation, the individual's body weight, age and general condition, and the particular formulation to be administered. The compositions may be applied to the skin in a single application or in multiple applications, preferably in two applications per day. Typical application quantities range from about one teaspoon to about 2 tablespoons. However, larger or small quantities may be applied as desired.

EXAMPLE

The effects of a magnesium-containing composition on DHEA levels in humans in accordance with the present invention were studied. Twenty subjects (18 female, 2 male) applied a lotion having the formulation shown in Table 1, below, twice daily for one month. Application quantities were approximately two teaspoons of lotion. DHEA-S serum levels and magnesium levels were measured before and after the study for all subjects. DHEA-S serum levels measured from blood samples were performed by the Core Endocrine Lab at Pennsylvania State University, Hershey, Pa. The DHEA-S serum measurements are accurate to within +2%. The results are shown in Table 2 below. As shown in Table 2, seventeen of the twenty subjects had an increased DHEA-S level after the study and eight of the twenty subjects for whom magnesium levels were measured showed an increase in magnesium levels. DHEA-S is present in quantities over ten times that of free DHEA. The results of this study suggest that reserves of DHEA, stored as sulfates, are increased by the methods disclosed herein. These methods offer great ease and safety for raising magnesium and DHEA levels in treated individuals. This is in marked contrast to oral administration of magnesium (e.g. magnesium taurate) which is difficult to absorb and does not increase DHEA levels.

TABLE 1

| COMPONENT | AMOUNT |
| --- | --- |
| magnesium chloride | one cup |
| water | three cups |
| methyl cellulose | two tablespoons |
| glycerin | two tablespoons |

TABLE 2

| Subject No. | Gender | Mg Level[a] Before Study | Mg Level After Study | DHEA-S Level[b] Before Study | DHEA-S Level After Study |
| --- | --- | --- | --- | --- | --- |
| 1 | F | 29.8 | 31.4 | 1275.2 | 1531.8 |
| 2 | F | 30.1 | 32.6 | 2906.6 | 3486.7 |
| 3 | M | 33.6 | 36.9 | 1091.3 | 1205.2 |
| 4 | F | 31.4 | 30.0 | 1000.4 | 1229 |
| 5 | M | 31.9 | 32.2 | 3055.3 | 2888.4 |

TABLE 2-continued

| Subject No. | Gender | Mg Level[a] Before Study | Mg Level After Study | DHEA-S Level[b] Before Study | DHEA-S Level After Study |
| --- | --- | --- | --- | --- | --- |
| 6 | F | 28.2 | 32.4 | 1275.8 | 1527.7 |
| 7 | F | 31.7 | 37.5 | 784.3 | 908.5 |
| 8 | F | 32.4 | 34.4 | 2411.2 | 2164.1 |
| 9 | F | 35.6 | 35.7 | 1582.4 | 1187.3 |
| 10 | F | 33.4 | 34.4 | 1225.5 | 1357.6 |
| 11 | F | 32.7 | 34.7 | 530.0 | 867.0 |
| 12 | F | 31.0 | 35.1 | 1331 | 1640 |
| 13 | F | 32.7 | 36.3 | 1438 | 1540 |
| 14 | F | 29.9 | 38.1 | 1299 | 1450 |
| 15 | F | 30.6 | 32.5 | 877 | 1163 |
| 16 | F | 26.6 | 29.9 | 415 | 500 |
| 17 | F | 29.5 | 32.4 | 2234 | 2925 |
| 18 | F | 31.8 | 36.4 | 540 | 769 |
| 19 | F | 30.3 | 43.7 | 2129 | 2173 |
| 20 | M | 29.5 | 31.5 | 1232 | 1458 |

[a]Magnesium serum level in mEq/liter (normal lab levels are 33.9-41.9)
[b]DHEA-S serum level in ng/ml (normal lab levels are 1500-5550 in males and 1000-3600 in females)

As discussed supra, Loria et al. demonstrated a strong correlation between enhanced immune response and serum DHEA levels. Loria et al. stated that increased serum DHEA levels could provide a very high amount of protection against many pathogenic viral, bacterial, and fungal infections, including opportunistic infections. It was also postulated that raising levels of DHEA in patient's serum is of value in the treatment of immunocompromised individuals suffering from AIDS or of those infected with the HIV virus showing the AIDS related complex (ARC).

Eich et. al, supra, demonstrated that elevated levels of DHEA and DHEA-S in patient's serum resulted in lower rates of platelet aggregation. It is well known that reducing the rate of platelet aggregation has significant health benefits, including, but not limited to, reduction in the incidence of mortality from vascular events such as a stroke, and also reduces the occurrence of restenosis following vascular interventions. Therefore, by raising serum DHEA levels in individuals via treatment utilizing the methods of the current invention, health benefits are expected.

It is understood that the invention is not confined to the particular embodiments set forth herein as illustrated, but embraces all such modifications thereof as come within the scope of the following claims.

What is claimed is:

1. A method of raising serum DHEA levels in an individual, the method comprising: (a) measuring the level of DHEA or DHEA-S in the individual; and (b) applying a therapeutically effective amount of a magnesium-containing composition to the individual's skin, the magnesium-containing composition consisting of about 25 to 35 weight percent magnesium chloride, water, a cellulose gelling agent and glycerin and further wherein the magnesium-containing composition is substantially free of sodium ions and sulfate ions.

2. The method of claim 1 wherein the cellulose is methyl cellulose.

3. The method of claim 1 wherein the magnesium-containing composition comprises about 60 to 75 weight percent water.

4. The method of claim 1 wherein the magnesium-containing composition comprises about 0.1 to 5 weight percent cellulose gelling agent.

5. The method of claim 1 wherein the magnesium-containing composition comprises about 0.1 to 5 weight percent glycerin.

6. A method of raising serum DHEA levels in an individual, the method comprising: (a) measuring the level of DHEA or DHEA-S in the individual; and (b) applying a therapeutically effective amount of a magnesium-containing composition to the individual's skin, the magnesium-containing composition consisting of about 25 to 35 weight percent magnesium chloride, about 60 to 75 weight percent water, about 0.1 to 5 weight percent methyl cellulose and about 0.1 to 5 weight percent glycerin and further wherein the magnesium-containing composition is substantially free of sodium ions and sulfate ions.

7. A composition for the transdermal absorption of magnesium consisting of:
   (a) about 25 to 35 weight percent magnesium chloride;
   (b) about 60 to 75 weight percent water;
   (c) about 0.1 to 5 weight percent of a cellulose gelling agent; and
   (d) about 0.1 to 5 weight percent glycerin.

8. The method of claim 1, further comprising measuring the level of DHEA, DHEA-S or magnesium in the individual after applying the magnesium-containing composition to the individual's skin.

9. The method of claim 1, wherein the magnesium-containing composition consists of about 25 to 35 weight percent magnesium chloride, about 60 to 75 weight percent water, about 0.1 to 5 weight percent methyl cellulose and about 0.1 to 5 weight percent glycerin.

10. The composition of claim 7, consisting of:
    (a) about 25 to 35 weight percent magnesium chloride;
    (b) about 60 to 75 weight percent water;
    (c) about 1 to 3 weight percent of a cellulose gelling agent; and
    (d) about 1 to 3 weight percent glycerin.

* * * * *